United States Patent
Boiteau et al.

(10) Patent No.: US 10,343,999 B2
(45) Date of Patent: Jul. 9, 2019

(54) METHOD FOR SYNTHESIZING ENANTIOMERICALLY PURE N-(PYRIDIN-4-YL)-2-HYDROXY-ALKYLAMIDE DERIVATIVES

(71) Applicant: GALDERMA RESEARCH & DEVELOPMENT, Biot (FR)

(72) Inventors: Jean-Guy Boiteau, Opio (FR); Sebastien Daver, Antibes (FR); Nicolas Rodeville, Mandelieu (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 15/780,164

(22) PCT Filed: Nov. 8, 2016

(86) PCT No.: PCT/EP2016/076962
§ 371 (c)(1),
(2) Date: May 30, 2018

(87) PCT Pub. No.: WO2017/092977
PCT Pub. Date: Jun. 8, 2017

(65) Prior Publication Data
US 2019/0010124 A1    Jan. 10, 2019

(30) Foreign Application Priority Data

Nov. 30, 2015 (FR) ...................... 15 61602

(51) Int. Cl.
| | | |
|---|---|---|
| C07D 213/75 | (2006.01) | |
| C07D 239/52 | (2006.01) | |
| C07C 51/02 | (2006.01) | |
| C07D 213/73 | (2006.01) | |

(52) U.S. Cl.
CPC ............ C07D 213/75 (2013.01); C07C 51/02 (2013.01); C07D 213/73 (2013.01); C07D 239/52 (2013.01)

(58) Field of Classification Search
CPC .................................................. C07D 213/75
USPC ......................................................... 546/292
See application file for complete search history.

(56) References Cited

U.S. PATENT DOCUMENTS 9,452,120 B2 * 9/2016 Poinsard ............. C07D 213/79
9,732,044 B2 * 8/2017 Poinsard ............. C07D 213/79

FOREIGN PATENT DOCUMENTS

WO     201080864  * 7/2010  .......... C07D 213/79
WO     2013064681 * 5/2013  .......... C07D 213/79

* cited by examiner

*Primary Examiner* — Taofiq A Solola
(74) *Attorney, Agent, or Firm* — Sunit Talapatra; Foley & Lardner, LLP

(57) ABSTRACT

The present invention relates to a novel process for preparing enantiomerically pure compounds of N-(pyrid-4-yl)-2-hydroxyalkylamide type corresponding to the general formula (C) below:

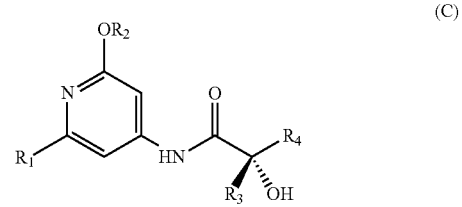

(C)

and also to processes for preparing the reaction intermediates used in this synthesis, said intermediates having the general formulae (A) and (B) below:

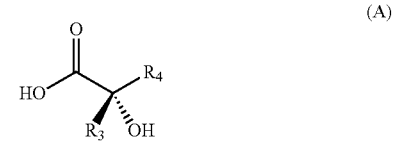

(A)

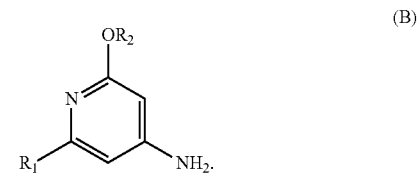

(B)

9 Claims, No Drawings

METHOD FOR SYNTHESIZING ENANTIOMERICALLY PURE N-(PYRIDIN-4-YL)-2-HYDROXY-ALKYLAMIDE DERIVATIVES

CROSS-REFERENCE TO PRIOR APPLICATIONS

This application is the U.S. National Stage of PCT/EP2016/076962, filed Nov. 8, 2016, (published in the French language on Jun. 8, 2017 as WO 2017/092977 A1; the title and abstract were also published in English), which claims priority under 35 U.S.C. § 119 of French Patent Application No. FR 1561602, filed Nov. 20, 2015, each hereby expressly incorporated by reference in its entirety and each assigned to the assignee hereof.

The present invention relates to a novel process for preparing enantiomerically pure compounds of N-(pyrid-4-yl)-2-hydroxyalkylamide type corresponding to the general formula (C) below:

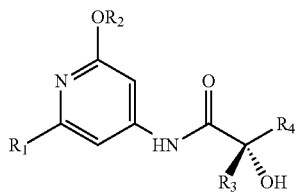

(C)

and also to processes for preparing the reaction intermediates used in this synthesis, said intermediates having the general formulae (A) and (B) below:

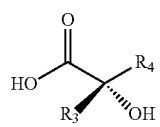

(A)

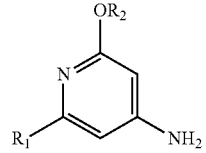

(B)

PRIOR ART

Patent application WO 2013/064681 discloses compounds that are powerful androgen receptor modulators, and which correspond to the general formula (I) below:

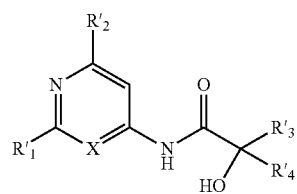

(I)

in which:

$R'_1$ represents a hydrogen atom, $R'_2$ represents a $C_1$-$C_6$ alkoxy, $R'_3$ and $R'_4$, which may be identical or different, represent a $C_1$-$C_{12}$ alkyl, X represents CH.

In said patent application, the compounds of general formula (I) in racemic form are prepared in one or two steps starting with the intermediate (III) according to method 1b or method 1a, respectively, according to reaction scheme 1 below:

Reaction scheme 1

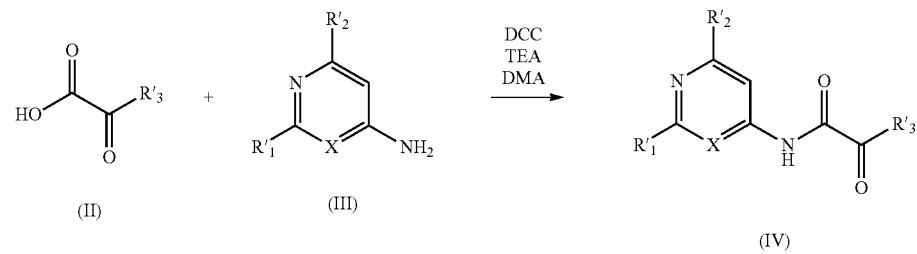

(II)  (III)  (IV)

Method 1a

R'4MgZ
Z = Br or Cl
or R'4Li
THF

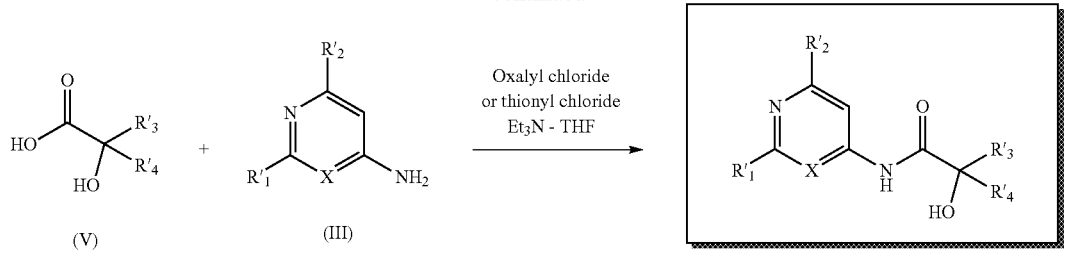

Method 1b

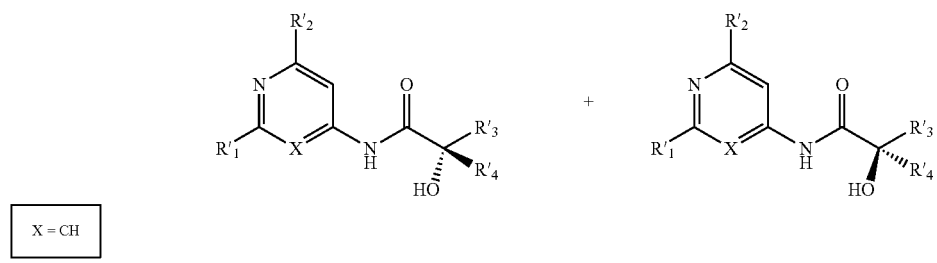

X = CH

The enantiomers corresponding to the racemic compounds of general formula (I) are prepared by separating and isolating each enantiomer from the racemic mixture of general formula (I) by preparative chiral HPLC under the conditions indicated in examples 71 to 80 of patent application WO 2013/064681.

This method for preparing the enantiomerically pure compounds of general formula (I) as described above, with the definitions of $R'_1$, $R'_2$, $R'_3$, $R'_4$ and X as indicated previously, does not make it possible to synthesize amounts of product greater than a gram. Specifically, in order to develop a larger-scale synthesis, the method disclosed in the prior art has the drawback of resorting to intermediate (III), the commercial availability of which on a kilogram scale is difficult.

In order to solve this problem, the Applicant developed a one-step microwave synthesis starting with commercial products of general formula (B4) in accordance with reaction scheme 2 below:

Reaction scheme 2

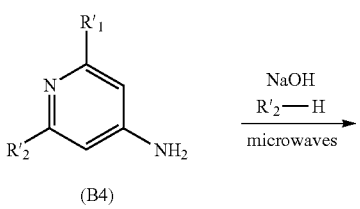

-continued

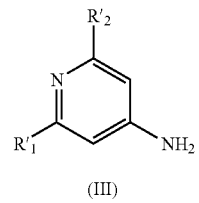

$R'_2$ = C1-C6 alkoxy

However, this synthesis still has two drawbacks. The commercial products of general formula (B4) are generally expensive and the use of microwaves can only be performed on a laboratory scale, making it necessary to repeat the operation several times in order to produce intermediate (III) on a kilogram scale.

Moreover, method 1a disclosed in patent application WO 2013/064681 also has the drawback of generating byproducts that are difficult to remove on account of the use of an excess of certain reagents, for instance dicyclohexylcarbodiimide (DCC).

Separation of the enantiomers on a preparative chiral phase is also another drawback of this method, since such a separation is difficult or even impossible to transpose to the scale of a kilogram and above.

Furthermore, the overall yield of these preparation methods is generally very low, less than 1%.

For all these reasons, there was thus a need for a method for preparing enantiomerically pure compounds corresponding to the general formula (I), said method being transposable to a large-scale (greater than a kilogram), making it possible to avoid the need for a chiral chromatography step, making it possible to obtain better yields and to obtain a product in crystalline form for the purpose of easier manipulation, and being economically viable.

BRIEF DESCRIPTION OF THE INVENTION

The Applicant thus solved these problems by developing a novel convergent synthetic process for preparing enantiomerically pure compounds corresponding to the general formula (C), starting with a chiral α-hydroxy acid intermediate of general formula (A) and an aromatic intermediate of general formula (B) according to reaction scheme 3 described below.

Coupling of the α-hydroxy acids with amines required the development of temporary protection of the alcohol function with a silyl group.

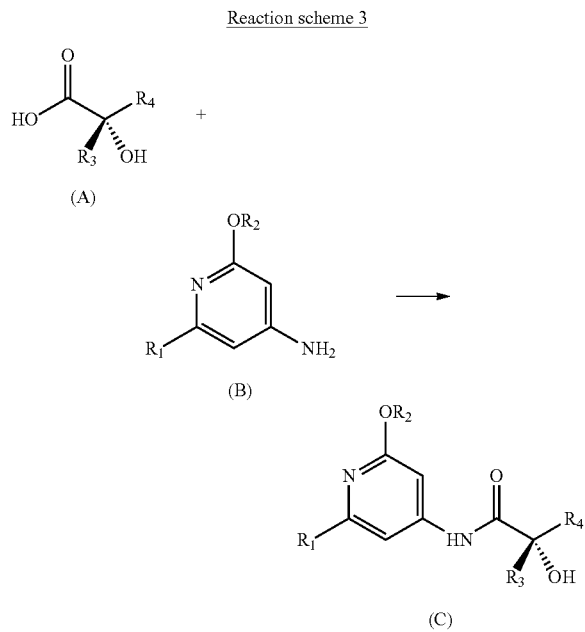

A first subject of the invention is thus a process for preparing an enantiomerically pure compound corresponding to the general formula (C),

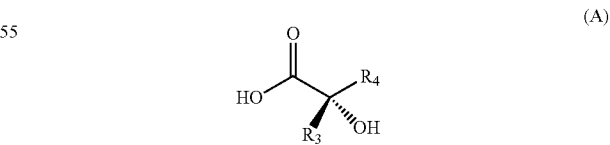

in which:
$R_1$ represents a halogen atom; preferably, $R_1$ is bromine,
$R_2$ represents a $C_1$-$C_4$ alkyl; preferably, $R_2$ is a methyl,
$R_3$ represents a $C_1$-$C_2$ alkyl; preferably, $R_3$ is a methyl,
$R_4$ represents a $C_3$-$C_6$ alkyl; preferably, $R_4$ is an isobutyl, and
said process comprising the following successive steps:
a) reacting in a halogenated solvent a chiral α-hydroxy acid of general formula (A)

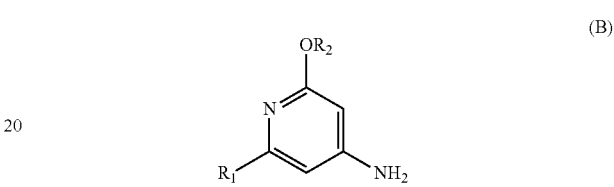

in the presence of a halotrialkylsilane and an organic amine base,
b) addition of N,N-dimethylformamide and of a carboxylic acid chlorinating agent between 0° and 5° C.,
c) addition of an aromatic intermediate of formula (B)

OR₂ (B)

(pyridine structure with $R_1$ and $NH_2$)

as a solution in a halogenated solvent in the presence of an organic amine base,
d) addition of an organic or mineral acid dissolved in an alcohol,
e) treatment of the reaction medium obtained in step d), comprising:
 i. a step of decantation followed by filtration of the organic phase over active charcoal, and
 ii. a step of crystallization, following the addition of a saturated hydrocarbon, of the enantiomerically pure compound corresponding to the general formula (C).

The process according to the invention leads to an enantiomerically pure compound corresponding to the general formula (C), for which the absolute configuration of the asymmetric carbon is R or S, preferably S.

This first embodiment has the advantage of achieving the synthesis of an enantiomerically pure compound corresponding to the general formula (I) on a kilogram scale and without the need for a chiral chromatography step. This synthetic method makes it possible to obtain a product in crystalline form, which facilitates the manipulation thereof. Furthermore, the yields are better than those obtained via the method described in patent application WO 2013/064681, which also makes the process more economically viable.

A second subject of the invention is a process, according to reaction scheme 5, for preparing the chiral α-hydroxy acid intermediate of general formula (A), (A)

(structure of α-hydroxy acid with $R_3$, $R_4$, OH)

in which formula:
$R_3$ represents a $C_1$-$C_2$ alkyl; preferably, $R_3$ is a methyl,
$R_4$ represents a $C_3$-$C_6$ alkyl; preferably, $R_4$ is an isobutyl, and
the absolute configuration of the asymmetric carbon is R or S, preferably S, said process comprising the following successive steps:

a) stirring a solution comprising a cyanating agent and a ketone of general formula (A1)

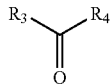
(A1)

in a solvent chosen from water and an organic solvent, optionally at a temperature of between 15 and 25° C. in the presence of a chiral catalyst such as ethylaluminum 2,2'-(((1E,1'E)-(((1R,2R)-cyclohexane-1,2-diyl) bis(azanylylidene)) bis(methanylylidene))bis-4-bromophenoxide (D) and N,N-dimethylaniline N-oxide as cocatalyst when the cyanating agent is a trialkylsilyl cyanide, b) adding a mineral acid until the intermediate cyanohydrin is hydrolyzed and production of the α-hydroxy acid of general formula (V),

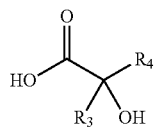
(V)

c) adding a chiral amine of structure (A2)

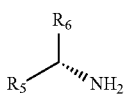
(A2)

in which $R_5$ represents a phenyl or a naphthyl, which is unsubstituted or substituted with a radical chosen from the list comprising a methyl, a methoxy, a halogen and a nitro, and $R_6$ represents a $C_1$-$C_3$ alkyl, until the salt of general formula (A3a) is obtained,

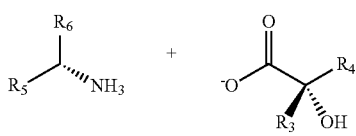
(A3a)

d) adding a mineral or organic acid until the chiral α-hydroxy acid of general formula (A) is obtained.

This second embodiment has the advantage of preparing the chiral α-hydroxy acid intermediate of general formula (A) without the need for a chromatography step on a chiral phase, such a step generally being difficult to transpose to the industrial scale and being expensive.

A third subject of the invention is a process, according to reaction scheme 6, for preparing the aromatic intermediate of general formula (B),

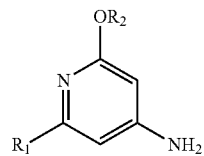
(B)

in which:

$R_1$ represents a halogen atom; preferably, $R_1$ is bromine, and $R_2$ represents a $C_1$-$C_4$ alkyl; preferably, $R_2$ is a methyl, said process comprising the following successive steps:

a) stirring a solution comprising citrazinic acid and a phosphoryl halide in sulfolane, b) introducing an alcohol $R_2$—OH until a dihalo intermediate product of general formula (B1) is obtained; $R_2$ representing a $C_1$-$C_4$ alkyl radical,

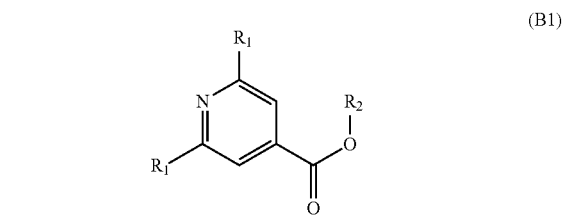
(B1)

c) heating the product obtained in step b) in the presence of an alkoxide $R_2O^-$ until an alkoxy intermediate product of general formula (B2) is obtained, $R_2$ representing a $C_1$-$C_4$ alkyl radical,

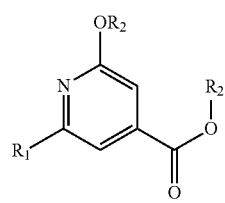
(B2)

d) reacting the product obtained in step c) in ammonia until an intermediate amide of general formula (B3) is obtained,

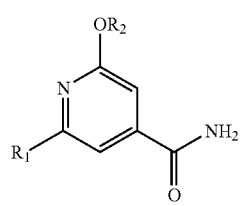
(B3)

e) reacting the product obtained in step d) with an aqueous solution of sodium hypochlorite in the presence of sodium hydroxide until the aromatic intermediate of general formula (B) is obtained.

This third embodiment has the advantage of affording access to the aminopyridine of formula (B) without using microwaves, which makes it possible to produce batches of several kilograms.

DETAILED DESCRIPTION OF THE INVENTION

Patent application WO 2013/064681 describes [examples 71 to 80] the preparation of the enantiomers corresponding to the racemic compounds of general formula (I).

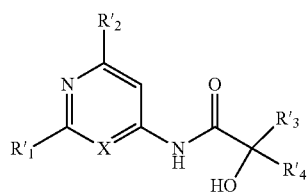
(I)

in which:
$R'_1$ represents a hydrogen atom,
$R'_2$ represents a $C_1$-$C_6$ alkoxy,
$R'_3$ and $R'_4$, which may be identical or different, represent a $C_1$-$C_{12}$ alkyl,
X represents CH.

These enantiomers are obtained after separation of the racemic mixture by preparative chiral HPLC according to reaction scheme 1 described previously.

This method has the drawback of not being extrapolable to an industrial scale. Moreover, it only allows the production of small amounts of each enantiomer, of the order of a gram. Furthermore, the enantiomers are obtained in oily form and are therefore not easy to manipulate.

In order to solve this problem, the Applicant developed a preparation method for directly obtaining the enantiomers corresponding to the racemic compounds of general formula (I) without the need for separation on a chiral column. This method has the advantage of obtaining large amounts of enantiomer (of the order of several tens of kilos) by performing several synthetic steps in the same reactor ("one-pot" reactions), without isolating the reaction intermediates and isolating the final enantiomer in crystalline form.

Thus, a first subject of the invention consists in preparing an enantiomerically pure compound corresponding to the general formula (C), in which:

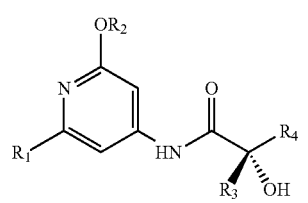
(C)

$R_1$ represents a halogen atom; preferably, $R_1$ is bromine,
$R_2$ represents a $C_1$-$C_4$ alkyl; preferably, $R_2$ is a methyl,
$R_3$ represents a $C_1$-$C_2$ alkyl; preferably, $R_3$ is a methyl,
$R_4$ represents a $C_3$-$C_6$ alkyl; preferably, $R_4$ is an isobutyl, and according to a process comprising the following successive steps:

a) reacting in a halogenated solvent a chiral α-hydroxy acid intermediate of formula (A):

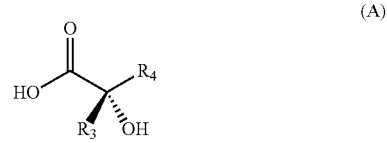
(A)

in the presence of a halotrialkylsilane and an organic amine base, b) addition of N,N-dimethylformamide and of a carboxylic acid chlorinating agent between 0° and 5° C., c) addition of an aromatic intermediate of formula (B):

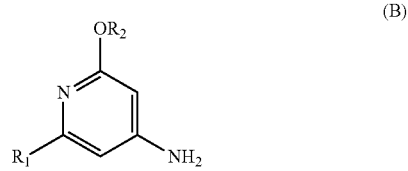
(B)

as a solution in a halogenated solvent in the presence of an organic amine base, d) addition of an organic or mineral acid dissolved in an alcohol, e) treatment of the reaction medium obtained in step d), comprising:

i. a step of decantation followed by filtration of the organic phase over active charcoal, and ii. a step of crystallization, following the addition of a saturated hydrocarbon, of the enantiomerically pure compound corresponding to the general formula (C).

The term "enantiomerically pure compound" refers to a compound in which the absolute configuration of the asymmetric carbon is R or S. In other words, the process according to the invention does not lead to a racemic mixture.

The process corresponding to this first subject of the invention is represented by reaction scheme 4 described below.

Reaction scheme 4

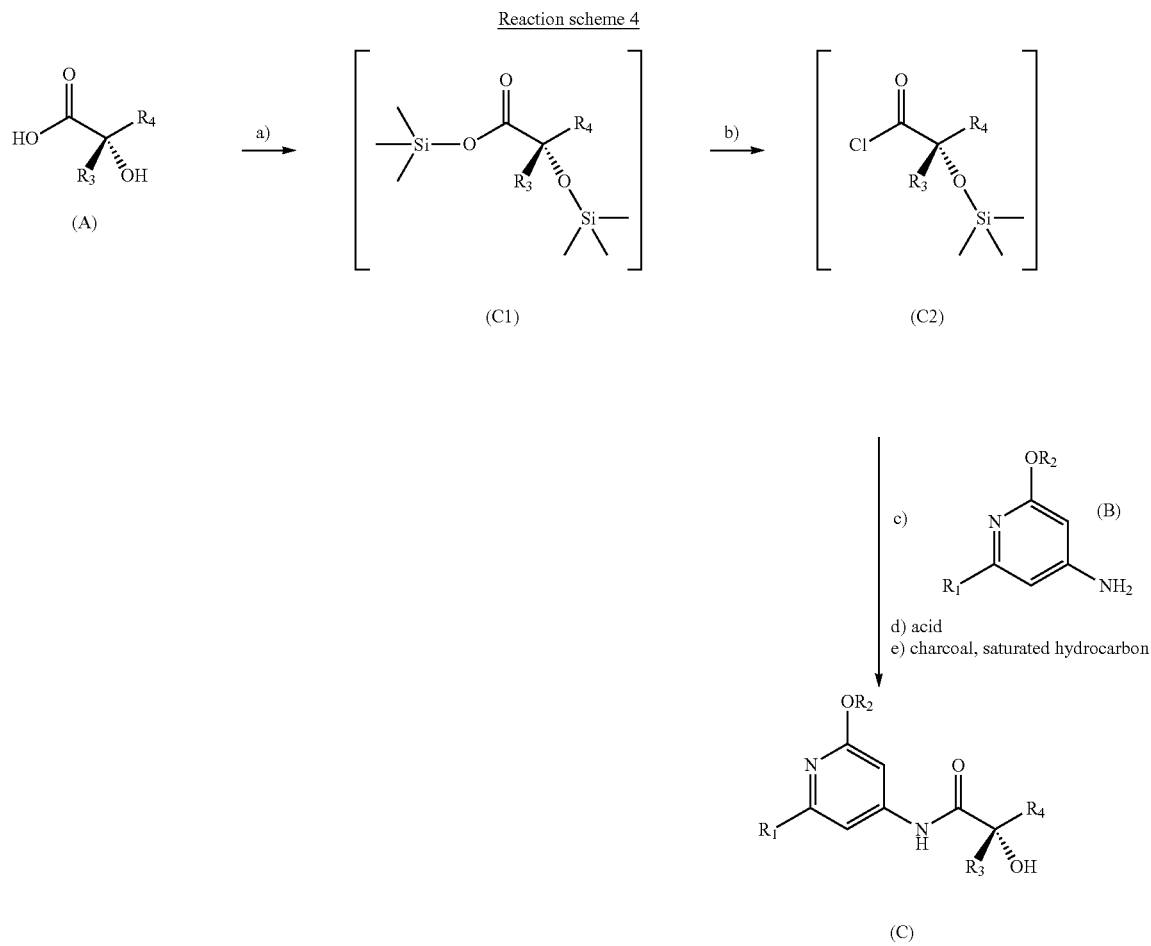

Step a) of this process is performed in a halogenated solvent.

The term "halogenated solvent" means a halogenated hydrocarbon, for example a chlorinated hydrocarbon, a fluorinated hydrocarbon or a hydrochlorofluorocarbon (HCFC, a group of molecules containing chlorine, fluorine and carbon). Examples of chlorinated solvents that may be mentioned include chloroform, chlorobenzene, le trichloroethylene (TCE), 1,2-dichloroethane, methylene chloride (dichloromethane), tetrachloroethylene (perchloroethylene) (PER) and 1,1,1-trichloroethane (methylchloroform).

Preferably, the chlorinated hydrocarbon is chosen from dichloromethane, chloroform, 1,2-dichloroethane and chlorobenzene.

Even more preferably, dichloromethane or DCM will be chosen.

During this step, the chiral α-hydroxy acid reaction intermediate (A), prepared beforehand, is dissolved in the halogenated solvent in the presence of an organic amine base.

The substituents $R_3$ and $R_4$ of the chiral α-hydroxy acid reaction intermediate (A) are chosen, respectively, from $C_1$-$C_2$ alkyls and $C_3$-$C_6$ alkyls.

Preferably, $R_3$ is a methyl and $R_4$ is an isobutyl. The configuration of the asymmetric centre is (S).

The term "organic amine base" means a cyclic or acyclic amine corresponding to the general formula RaRbRcN, in which Ra, Rb and Rc represent hydrocarbon-based radicals which may or may not form a ring with the nitrogen atom. Examples that may be mentioned include tributylamine, triethylamine, pyridine, 4-dimethylaminopyridine and diisopropylethylamine.

The organic amine base is preferably 4-dimethylaminopyridine or DMAP.

During this step, a halotrialkylsilane is added to the reaction medium so as to temporarily protect the alcohol function.

The term "halotrialkylsilane" means a C1-C4 trialkyl silyl halide. Examples that may be mentioned include trimethylsilyl chloride, triethylsilyl chloride, triisopropylsilyl chloride and tert-butyldimethylsilyl chloride.

Trimethylsilyl chloride or TMSCl is preferably used.

The addition of the halotrialkylsilane is preferably performed at a temperature of between 0° C. and 5° C.

Step b) of this process is performed without isolating the intermediate product (C1) obtained in step a).

During step b), N,N-dimethylformamide and a carboxylic acid chlorinating agent are added to the reaction medium, which is then stirred for 1 to 2 hours between 5° and 20° C.

The addition of the carboxylic acid chlorinating agent is preferably performed at a temperature of between 0° C. and 5° C.

The term "carboxylic acid chlorinating agent" means any reagent which makes it possible to obtain an acyl chloride from a carboxylic acid. Examples of such chlorinating agents that may be mentioned include thionyl chloride, phosphorus trichloride, phosphorus pentachloride and oxalyl chloride.

Preferably, the chlorinating agent is oxalyl chloride or thionyl chloride.

Step c) consists in adding the aromatic reaction intermediate (B) in a halogenated solvent and in the presence of an organic amine base as described previously.

Dichloromethane is preferred as halogenated solvent and pyridine is preferred as organic amine base.

The substituents R1 and R2 of the aromatic reaction intermediate (B) are chosen, respectively, from a halogen atom and a $C_1$-$C_4$ alkyl. Bromine will be preferred as halogen and methyl as $C_1$-$C_4$ alkyl.

During step d), a solution of an organic or mineral acid dissolved in an alkanol is added to the reaction medium, preferably while maintaining the temperature below 25° C.

The term "organic acid" means an aliphatic or aromatic carboxylic acid.

Examples that may be mentioned include acetic acid, citric acid, trifluoroacetic acid, trichloroacetic acid, lactic acid and benzoic acid.

The organic acid is preferably acetic acid.

The term "mineral acid" means an acid derived from an inorganic mineral.

Among the mineral acids, mention may be made especially of hydrochloric acid, sulfuric acid and nitric acid.

The mineral acid is preferably hydrochloric acid.

The term "alcohol" means a linear or branched alcohol containing from 1 to 6 carbon atoms. Examples that may be mentioned include ethanol, isopropanol and propanol.

Preferably, the alcohol is ethanol.

The final step e) of this process consists in working up the reaction medium so as to isolate the enantiomerically pure compound corresponding to the general formula (C). This step optionally comprises a step of adding an aqueous solution of a mineral acid to the reaction medium obtained in step d).

Hydrochloric acid is preferably used.

After stirring and separating the medium by settling, the organic phase is separated out and washed successively with water, sodium hydroxide and water. It is then clarified on active charcoal and concentrated by distilling off the solvents.

A saturated hydrocarbon is then added to the clarified organic phase, the medium is refluxed to distil off some more of the solvents, and it is then cooled to between 20° and 30° C.

The enantiomerically pure compound corresponding to the general formula (C) crystallizes. It is isolated by filtration.

The term "saturated hydrocarbon" means a cyclic or acyclic alkane, which is liquid at room temperature.

Preferably, the saturated hydrocarbon is a cyclic or acyclic $C_5$-$C_{12}$ alkane.

Examples that may be mentioned include pentane, hexane, heptane, octane, cyclohexane, 1,2-dimethylcyclohexane and 1-ethyl-3-methylcyclopentane.

Cyclohexane will preferably be chosen.

Thus, one of the advantages of this process is that several consecutive steps are performed "in one pot", without isolating any reaction intermediate, and that the enantiomerically pure compound corresponding to the general formula (C) is obtained directly in crystalline form, without the need for a chiral chromatography step, in yields of greater than 65% and amounts of the order of several kilograms.

According to a particular embodiment, it will be preferred to perform the process as described for this first subject of the invention with $R_1$ representing a bromine atom, $R_2$ representing a methyl, $R_3$ representing a methyl and $R_4$ representing an isobutyl. The absolute configuration of the asymmetric centre is (S).

A second subject of the invention is a process for preparing the chiral α-hydroxy acid intermediate of general formula (A),

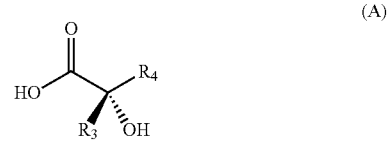

(A)

in which:
$R_3$ represents a $C_1$-$C_2$ alkyl; preferably, $R_3$ is a methyl,
$R_4$ represents a $C_3$-$C_6$ alkyl; preferably, $R_4$ is an isobutyl,
the absolute configuration of the asymmetric carbon is R or S, preferably S,
said process comprising the following successive steps:
a) stirring a solution comprising a cyanating agent and a ketone of general formula (A1)

(A1)

in a solvent chosen from water and an organic solvent, optionally in the presence of a chiral catalyst such as ethylaluminum 2,2'-((1E,1'E)-(((1R,2R)-cyclohexane-1,2-diyl) bis(azanylylidene)) bis(methanylylidene))bis-4-bromophenoxide (D) and N,N-dimethylaniline N-oxide as cocatalyst when the cyanating agent is a trialkylsilyl cyanide, at a temperature of between 15 and 25° C.,
b) adding a mineral acid until the intermediate cyanohydrin is hydrolyzed and production of the α-hydroxy acid of general formula (V),

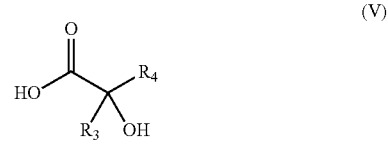

(V)

c) adding a chiral amine of structure (A2)

(A2)

in which
$R_5$ represents a phenyl or a naphthyl aromatic ring, which is unsubstituted or substituted with a radical chosen from the list comprising a methyl, a methoxy, a halogen and a nitro, and
$R_6$ represents a $C_1$-$C_3$ alkyl,
until the salt of general formula (A3a) is obtained,

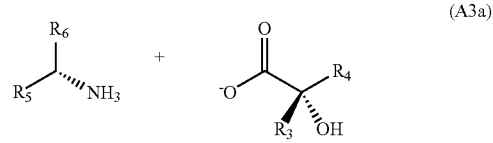

(A3a)

d) adding a mineral or organic acid until the chiral α-hydroxy acid of general formula (A) is obtained.

The process corresponding to this second subject of the invention is represented by reaction scheme 5.

Reaction scheme 5

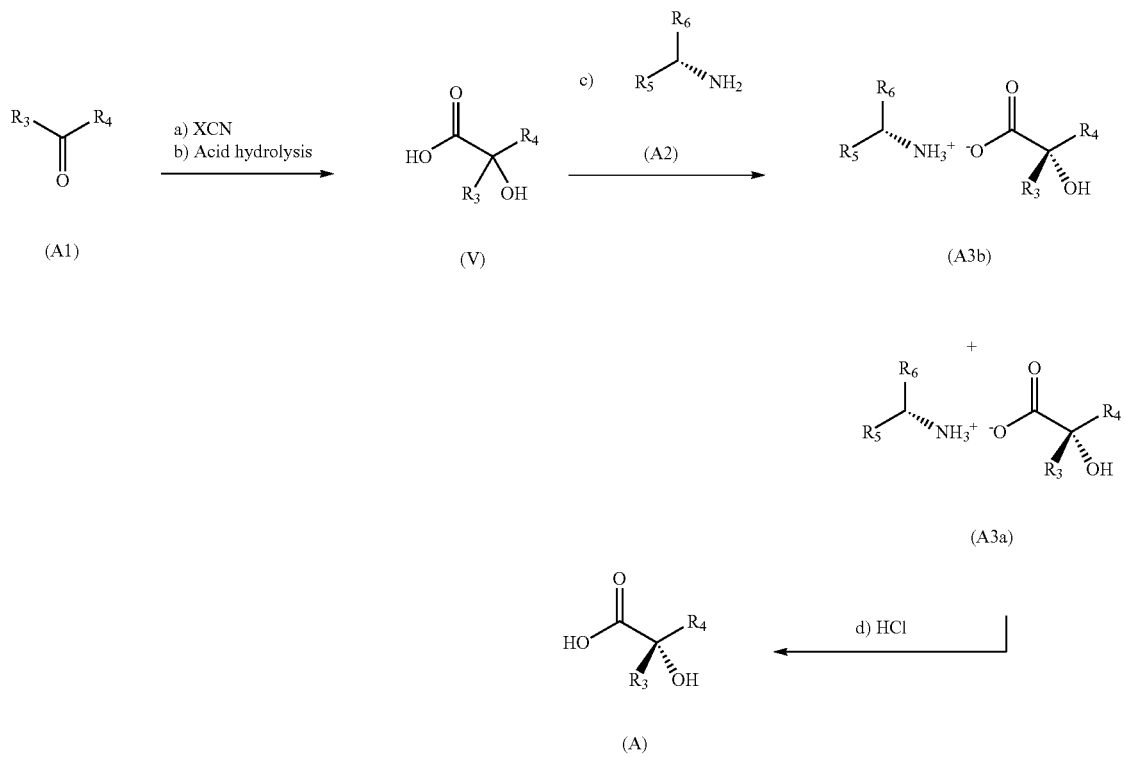

In this process, step a) consists in performing cyanation of the starting ketone (A1) and step b) consists in hydrolyzing in acidic medium the cyanohydrin obtained as intermediate so as to obtain the α-hydroxy acid of general formula (V).

Two particular embodiments may be followed regarding step a).

In a first embodiment, the ketone (A1) is reacted with a cyanating agent in water or in a halogenated solvent as defined previously.

The term "cyanating agent" means a cyanide of formula XCN in which X represents a sodium or potassium atom or a trialkylsilyl radical.

Preferably, the cyanating agent is sodium cyanide.

This first embodiment makes it possible to obtain, after acidic hydrolysis (step b)), for example using sulfuric acid or hydrochloric acid, a racemic mixture of the α-hydroxy acid of general formula (V).

In a second embodiment, when the cyanating agent is a trialkylsilyl halide, a chiral metal catalyst, the ligand of which has the structure (A4a) or (A4b) below, is used to induce an enantiomeric excess of the α-hydroxy acid of general formula (V) after hydrolysis of the cyanohydrin:

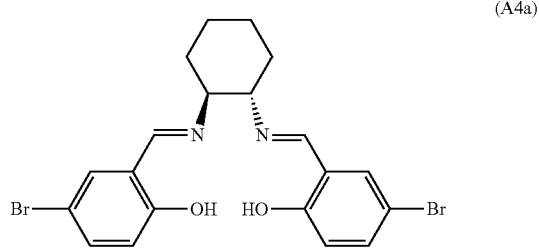

(A4a)

-continued

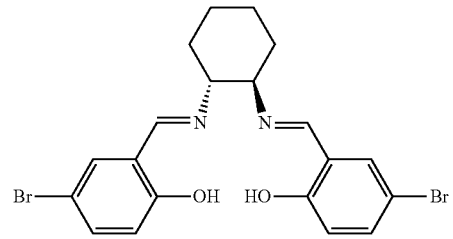

(A4b)

The preferred trialkylsilyl cyanide is trimethylsilyl cyanide. Aluminum is the preferred metal to use with the ligand of structure (A4a) or (A4b) to form the chiral metal catalyst.

The preferred chiral metal catalyst is ethylaluminum 2,2'-((1E,1'E)-(((1R,2R)cyclohexane-1,2-diyl)bis(azanylylidene))bis(methanylylidene))bis-4-bromophenoxide (D)

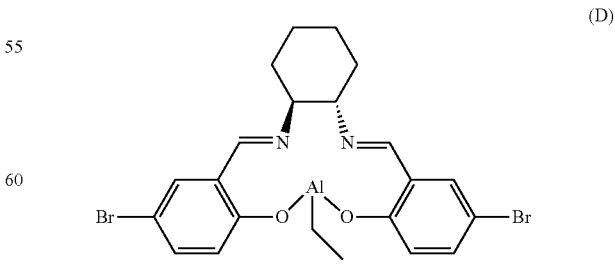

(D)

A cocatalyst of N-oxide type is also used at the same time as the chiral metal catalyst whose ligand has the structure (A4).

The cocatalysts of N-oxide type that may be used in this embodiment are described in Fu-Xue Chen et al., *Chem. Eur. J.*, 2004, 74, 4790-4797.

Examples that may be mentioned include trimethylamine N-oxide, N-methylmorpholine N-oxide, N,N-dimethylaniline N-oxide, N,N-dimethyl-2-methylaniline N-oxide and N,N-dimethylcyclohexylamine N-oxide. N,N-Dimethylaniline N-oxide will be preferred.

The publication by Fu-Xue Chen et al. describes enantioselective cyanosilylation reactions of ketones catalyzed with aluminum complexes and an N-oxide.

Said publication describes aluminum ligands corresponding to the general formula (A5) below in which Ra and Rb are chosen from H, tBu, Me, Cl, adamantanyl, MeO, Ph and Br:

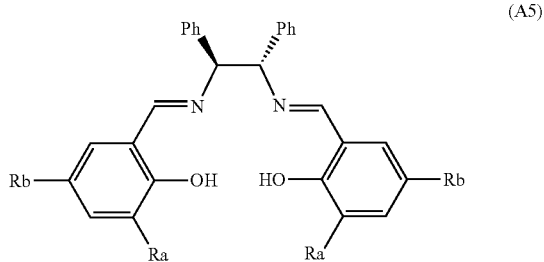

Although these ligands of formula (A5) give the best enantiomeric excesses (between 73% and 88%) described in table 2 of the publication by Fu-Xue Chen et al. starting with acetophenone, no significant enantiomeric excess was detected in the context of the present invention on ketones of structure (A1) for which the substituents R3 and R4 are, respectively, C1-C2 alkyls and C3-C6 alkyls. (1.5% e.e. obtained with ligand A5 complexed with aluminum in which Rb=Br and Ra=H).

However, although the publication by Fu-Xue Chen et al. describes poorer enantiomeric excesses (51%; table 2) with the ligand of structure (A6), it is with the ligand of structure (A4a) or (A4b) complexed with aluminum that we obtained the best results, said ligand (A4a) or (A4b) not being described or suggested in the publication by Fu-Xue Chen et al.

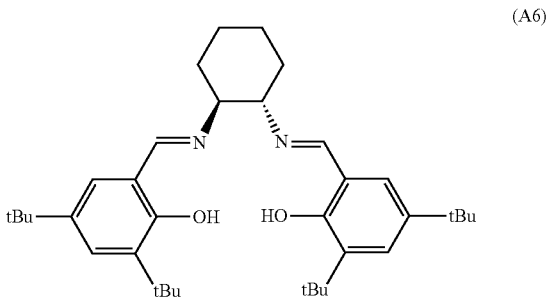 [SMILES: CC(C)(C)c1cc(/C=N/[C@H]2CCCC[C@@H]2/N=C/c2cc(C(C)(C)C)cc(C(C)(C)C)c2O)c(O)c(C(C)(C)C)c1]

Moreover, the publication by Fu-Xue Chen et al. indicates that temperatures of the order of −20° C. need to be used to perform these enantioselective cyanosilylation reactions of ketones. In the context of the present invention, the results obtained (yield, enantiomeric excess) after steps a) and b) of this second embodiment are better when the temperature is about +20° C. rather than about −20° C. Better results are obtained at temperatures above 15° C.

Preferably, the temperature used during steps a) and b) is between 15 and 25° C. and even more preferably between 20 and 23° C.

This second embodiment makes it possible, after acidic hydrolysis (step b)), to obtain a mixture of the α-hydroxy acid of general formula (V) enantiomerically enriched in one of the two enantiomers, the formation of the predominant enantiomer being associated with the use of a chiral catalyst. The enantiomeric excess obtained is between 40% and 90%, preferably between 50% and 70%.

Step c) consists in separating the enantiomers of the α-hydroxy acid of general formula (V) obtained in racemic form or in enriched form and in isolating one of the two enantiomers. This is referred to as resolution of enantiomers. This resolution is induced with an optically pure auxiliary of structure (A2), i.e. a mixture of the enantiomers of the α-hydroxy acid of general formula (V) is reacted with this optically pure auxiliary of structure (A2). In this case, the mixture of enantiomers (V) becomes a mixture of two diastereoisomers of structures (A3a) and (A3b), which may be separated more readily via conventional physicochemical techniques such as crystallization. Diastereoisomer (A3a) is insoluble and crystallizes preferentially relative to diastereoisomer (A3b), which remains in solution.

In the case of the present invention, the optically pure auxiliary is a chiral amine of structure (A2). This optically pure chiral amine is chosen, for example, from the list comprising α-methylbenzylamine (α-MBA) or 1-phenylethylamine, α-ethylbenzylamine (α-EBA), threo-2-amino-1-(p-nitrophenyl)-1,3-propanediol (TANP), 1-(2-naphthyl)ethylamine (NEA), phenylglycine and also a sodium, potassium or lithium salt of phenylglycine. (S)-1-Phenylethylamine (α-MBA; structure (A2) for which R5 represents a phenyl and R6 represents a methyl) or (R)-1-(2-naphthyl)ethylamine (NEA; structure (A2) for which $R_5$ represents a naphthyl and R6 represents a methyl) will be preferred. The preferred chiral amine of structure (A2) is (S)-1-phenylethylamine.

The mole ratio between the α-hydroxy acid of general formula (V) and the chiral amine of structure (A2) is preferably of the order of 1.

When the α-hydroxy acid of general formula (V) obtained in step b) is a racemic mixture, the use of one molar equivalent of chiral amine of structure (A2) makes it possible to obtain a mixture diastereomerically enriched in compound (A3a). A single recrystallization of the preceding mixture in a solvent such as ethyl acetate is sufficient to obtain the enantiomerically pure compound (A3a).

Step d) consists in hydrolyzing the diastereoisomer of formula (A3a) in the presence of a mineral acid so as to generate the enantiomerically pure chiral α-hydroxy acid of general formula (A).

When the α-hydroxy acid of general formula (V) obtained in step b) is a mixture enriched in one of the two enantiomers, the addition of one molar equivalent of chiral amine of structure (A2) makes it possible to obtain, after crystallization, the enantiomerically pure diastereoisomer (A3a). However, this particular embodiment also has the advantage of leading to a better mass yield.

A third subject of the invention is a process, according to scheme 3, for preparing the aromatic intermediate of general formula (B),

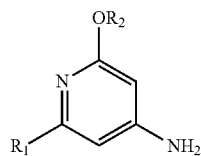
(B)

in which:
R$_1$ represents a halogen atom, preferably bromine, and
R$_2$ represents a C$_1$-C$_4$ alkyl, preferably a methyl,
said process comprising the following successive steps:

a) stirring a solution comprising citrazinic acid and a phosphoryl halide PO(R$_1$)$_3$ in sulfolane, b) introducing an alcohol R$_2$—OH until the dihalo intermediate product of general formula (B1) is obtained, R$_2$ representing a C$_1$-C$_4$ alkyl radical,

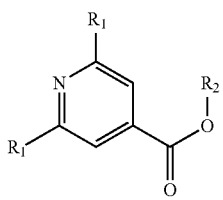
(B1)

c) heating the product obtained in step b) in the presence of an alkoxide R$_2$O$^-$ until an alkoxy intermediate product of general formula (B2) is obtained, R$_2$ representing a C$_1$-C$_4$ alkyl radical,

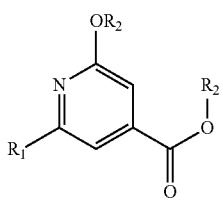
(B2)

d) reacting the product obtained in step c) in ammonia until an intermediate amide of general formula (B3) is obtained,

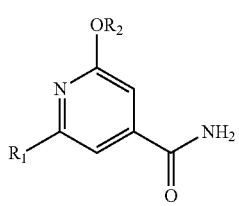
(B3)

e) reacting the product obtained in step d) with an aqueous solution of sodium hypochlorite in the presence of sodium hydroxide until the aromatic intermediate of general formula (B) is obtained.

The process corresponding to this third subject of the invention is represented by reaction scheme 6.

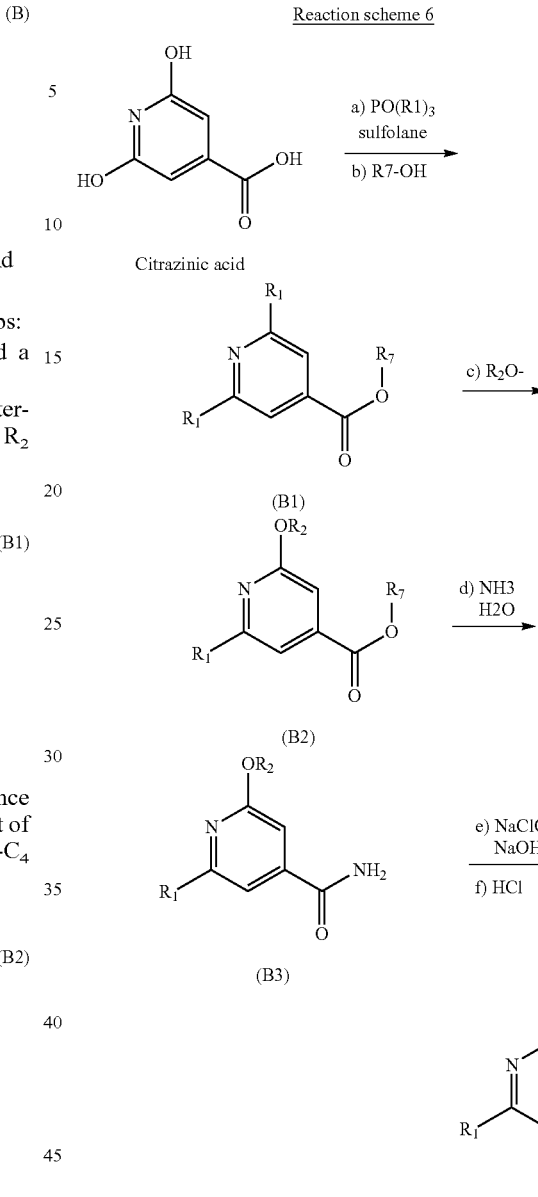

In this process, step a) consists in performing a halogenation of citrazinic acid in the presence of a phosphoryl halide PO(R$_1$)$_3$ and sulfolane.

By way of example, the phosphoryl halides used are phosphoryl bromide or chloride. Phosphoryl bromide will be preferred.

The amount of phosphoryl used is preferably between 1 and 4 molar equivalents relative to the citrazinic acid, preferably between 1.5 and 3 and even more preferably 1.5.

The temperature is preferably between 90° C. and 140° C., preferably between 120° C. and 130° C., and even more preferably it is 125° C.

The amount of sulfolane used is between 2.5 and 8 volumes of sulfolane relative to the citrazinic acid. One volume corresponds to 1 liter of solvent per kilo of citrazinic acid. 5 volumes of sulfolane will preferably be used.

The preferred conditions for this first step are:
1 molar equivalent of citrazinic acid,
1 to 2 molar equivalents of phosphoryl bromide, preferably 1.5 molar equivalents,
4 to 6 volumes of sulfolane, preferably 5 volumes.

The use of sulfolane has the advantage of controlling the exothermicity of this reaction and of having a better impurity profile.

The use of a limited volume facilitates the isolation of intermediate (B1) in the following step b).

Specifically, step b) is performed directly on the reaction medium obtained in step a).

During step b), a $C_1$-$C_4$ alcohol $R_2$—OH is introduced into the reaction medium.

Examples of alcohols used that may be mentioned include methanol, ethanol, n-propanol, isopropanol and n-butanol. Alcohols with a low boiling point will be preferred, preferably methanol.

Step b) allows intermediate (B1) or alkyl 2,6-dihaloisonicotinate to be obtained.

By using the preferred conditions above, the preferred intermediate (B1) obtained is methyl 2,6-dibromoisonicotinate.

Step c) consists in replacing only one of the two halogens of intermediate (B1) with a $C_1$-$C_4$ alkoxide R2O—. This reaction is performed in the presence of 1 molar equivalent of alkoxide R2O— in an organic ether solvent.

Examples of sources of alkoxide that may be mentioned include sodium or potassium methoxide or ethoxide in ether solution. Examples of ether solvents that may be mentioned include tetrahydrofuran (THF) and methyltetrahydrofuran (MeTHF). The solutions are commercial or may be prepared according to methods that are well known to those skilled in the art.

The temperature of this reaction is between 40° C. and 70° C., preferably 60° C. This reaction allows intermediate (B2) or alkyl 2-halo-6-alkoxyisonicotinate to be isolated.

The preferred alkoxide is sodium methoxide.

Starting with the preferred intermediate (B1) described above, namely methyl 2,6-dibromoisonicotinate, the preferred intermediate (B2) is methyl 2-bromo-6-methoxyisonicotinate.

Step d) consists in converting the ester function of intermediate (B2) into an amide function.

This step d) is performed in the presence of ammonia. The amide formed is generally insoluble in the medium, which allows it to be filtered off. The intermediate 2-halo-6-alkoxyisonicotinamide of structure (B3) is thus isolated.

Starting with the preferred intermediate (B2) described above, namely methyl 2-bromo-6-methoxyisonicotinate, the preferred intermediate (B3) is methyl 2-bromo-6-methoxyisonicotinamide.

Intermediate (B3) is reacted in the next step e), which consists in converting the amide function of (B3) into an amine function. This step is performed in water in the presence of sodium hydroxide. An aqueous solution of sodium hypochlorite is added to the reaction medium while maintaining the temperature between 0° C. and 10° C. The reaction medium is then heated to between 50° C. and 80° C. until conversion of the amide (B3) is complete. The reaction medium is then cooled to between 0° C. and 10° C., and then acidified by adding hydrochloric acid solution.

The 2-halo-4-amino-6-alkoxypyridine of structure (B) precipitates in the reaction medium. It is isolated by filtration.

Starting with the preferred intermediate (B3) described above, namely 2-bromo-6-methoxyisonicotinamide, the preferred intermediate (B) is methyl 2-bromo-4-amino-6-methoxypyridine.

The examples that follow illustrate the invention, but do not limit it in any way. The structures of the compounds described were confirmed by usual spectroscopic techniques.

EXAMPLES

Example 1

Preparation of 2-bromo-4-amino-6-methoxypyridine

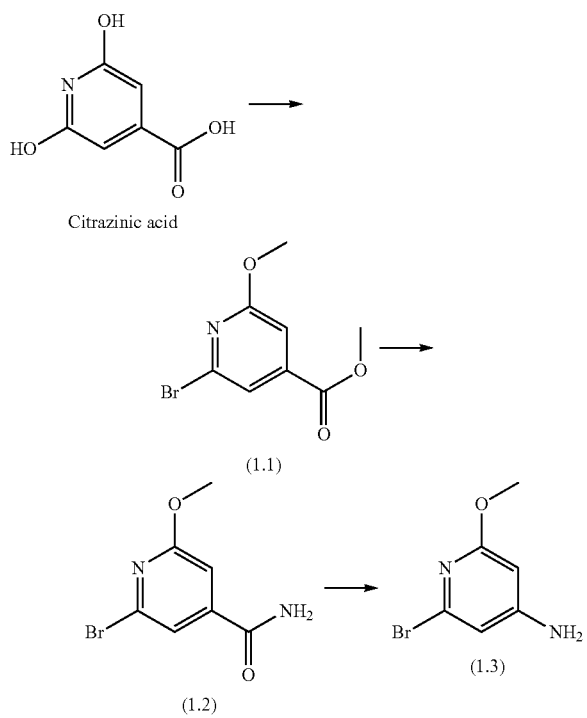

Step 1: Synthesis of methyl 2-bromo-6-methoxyisonicotinate (1.1)

Citrazinic acid (1.0 kg, 6.4 mol, 1 eq.) and sulfolane (6.3 kg, 5 vol.), melted beforehand (in an oven at 60° C.), are placed in a 20 L reactor. The reaction medium is stirred at a temperature of 90° C. and a solution of POBr3 (2.77 kg, 9.7 mol, 1.5 eq.) in sulfolane (3.53 kg, 2.8 vol.), prepared beforehand, is then introduced over 39 minutes. [Ti=93.3° C.→m.p.=89.0° C.]. The reaction medium is stirred at a temperature of 125° C. for 2 hours at this temperature. The reaction progress is monitored by HPLC: disappearance of the citrazinic acid. The reaction medium is cooled to a temperature of 40° C., and methanol (2.61 L, 10 eq.) is then introduced over 30 minutes (Ti=43.9° C.→m.p.=47.0° C.]. The reaction medium is stirred at 45° C. for 30 minutes and the methanol is distilled off under vacuum (V=0.64 L). The reaction medium (m=13.38 kg) is placed in a suitable container.

Water (8.0 kg, 8 vol.) is placed in a 20 L reactor, and the preceding reaction medium is then introduced at 20° C. so as to precipitate the crude intermediate product. The reaction medium is cooled to a temperature of 0° C. and then stirred at this temperature for 1 hour. The solid is filtered off and rinsed with water (4×3 L). The product is loaded back into the reactor and MeTHF (4.30 kg, 5 vol.) is then added, along with 0.68 kg of active charcoal. The reaction medium is heated at 50° C. and left stirring at this temperature for 30 minutes. The reaction medium is filtered through Clarcel® and then rinsed with dichloromethane (3×1 L) and then rinsed with MeTHF (4×1.7 kg). The organic phase is washed with saturated NaCl solution (1.0 L, 1 vol.).

The organic phase is codistilled with MeTHF (8 L) until the water content reaches 0.03%. Production of 4.84 kg of a solution of methyl 2,6-dibromoisonicotinate in MeTHF (mass assay at 20.45% w/w by HPLC—external calibration—i.e. 0.99 kg of methyl 2,6-dibromoisonicotinate). Mass yield=52%, HPLC purity=94%.

The solution of methyl 2,6-dibromoisonicotinate (4.84 kg, KF=0.03% w/w) is placed in a 20 L reactor and the reaction medium is then heated to 60° C. A solution of NaOMe at 25% w/w in MeTHF (0.73 kg, 6.5 mol, 1 eq.) is introduced over 58 minutes [Ti=59.3° C.→m.p.=65.5° C.]. A sample is taken for HPLC analysis: 87.5% of methyl 2-bromo-6-methoxyisonicotinate. The reaction medium is cooled to 30° C. and then washed successively with saturated NaHCO$_3$ solution (8.0 L) and then again with saturated NaHCO$_3$ solution (2.0 L) and finally with saturated NaCl solution (3.0 L). The organic phase is distilled off and the residue (m=0.90 kg) is then taken up in isopropanol (5.0 L), heated to reflux and cooled to 20° C. (start of crystallization observed at 45° C.) and then to 0° C. The solid is filtered off and rinsed with isopropanol (1.2 L). The solid is dried in a vacuum oven at 45° C. to constant mass. Production of 691 g of methyl 2-bromo-6-methoxyisonicotinate. Yield=44%. HPLC purity=>99.0%.

1H NMR (400 MHz, CDCl$_3$): 7.58 (s, 1H); 7.26 (s, 1H); 3.96 (s, 3H), 3.93 (s, 3H).

Step 2: Synthesis of 2-bromo-6-methoxyisonicotinamide (1.2)

The methyl 2-bromo-6-methoxyisonicotinate (450 g; 1.83 mol; 1.00 eq.) is placed in a 10 L reactor, followed by addition of 6.4 M aqueous ammonia solution (4 L). The suspension is stirred at T=20° C. for 48 hours and then filtered, and the cake is washed with water (7×900 ml) until the washing waters reach pH=8. The solid is dried in a ventilated oven at 40° C. 370 g of 2-bromo-6-methoxyisonicotinamide are obtained. (Yield=87%)

1H NMR (400 MHz, DMSO-d$_6$): 8.24 (bs, 1H); 7.82 (bs, 1H); 7.58 (s, 1H); 7.23 (s, 1H), 3.89 (s, 3H).

Step 3: Synthesis of 2-bromo-4-amino-6-methoxypyridine (1.3)

2-Bromo-6-methoxyisonicotinamide (100 g; 0.44 mol; 1.00 eq.) and water (400 ml) are placed in a 1 L jacketed reactor and the reaction mixture is cooled to 10° C. A sodium hydroxide solution is prepared by dissolving NaOH (21 g, 0.51 mol) in 50 mL of water, and this solution is then added while maintaining the temperature below 10° C. A sodium hypochlorite solution (279 ml; 139.50 g/L; 0.52 mol; 1.2 eq.) is added while maintaining the temperature below 10° C. and the reaction mixture is then stirred at 20° C. for 2 hours at this temperature.

NaOH (20.96 g; 0.51 mol; 1.16 eq.) is dissolved in 400 mL of water in a 4-L jacketed reactor, and this solution is then heated to 80° C. The chloramine solution (about 800 mL) is added to this sodium hydroxide solution over 20 minutes (T end of addition=77° C.) and the reaction mixture is stirred for 2 hours at 80° C. and then cooled to 25° C. Water (700 mL) and then ethanol (100 mL) are added to the reaction medium and the mixture is then cooled to 10° C. 36% hydrochloric acid solution (140 ml; 12 M; 1.69 mol; 3.88 eq.) is added while maintaining the temperature below 6° C. and the reaction mixture is then warmed to 20° C. 36% hydrochloric acid solution (36 ml; 12 M; 0.44 mol; 1.00 eq.) in 500 mL of water is added to the reaction medium. The solid is filtered off on dicalite and then placed in a 4 L reactor. Sodium hydroxide (NaOH; 99.90 g; 2.42 mol; 5.55 eq.) is added portionwise while maintaining the temperature below 30° C. The reaction mixture is stirred for 1 hour at 25° C. and then filtered. The solid is washed with 3×1 L of water and then dried in a ventilated oven at 45° C. 76 g of 2-bromo-4-amino-6-methoxypyridine are obtained (yield=86%)

1H NMR (400 MHz, DMSO-d$_6$): 6.37 (s, 1H); 6.27 (bs, 2H); 5.81 (s, 1H); 3.70 (s, 3H).

Example 2

Preparation of (S)-2-hydroxy-2,4-dimethylpentanoic Acid

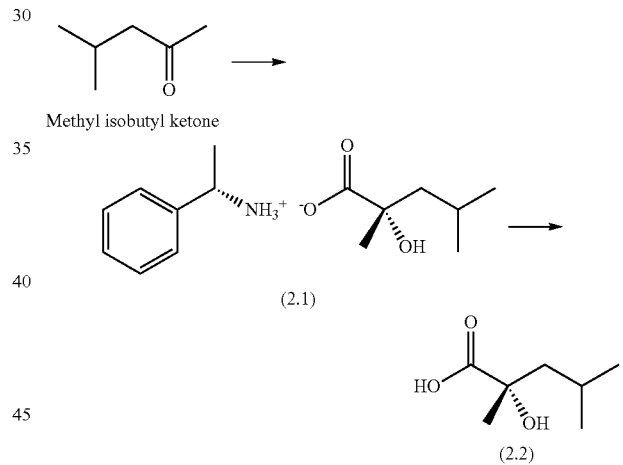

Step 1: Synthesis of (S)-1-phenylethylammonium (S)-2-hydroxy-2,4-dimethylpentanoate (2.1)

Sodium cyanide (200 kg, 4081 mol) and water (469 kg) are placed in a 2500 L reactor, the solution is cooled to 5° C. and methyl isobutyl ketone (402 kg, 4020 mol) is then added while maintaining the temperature at 5° C. The reaction mixture is stirred for 1 hour at 5° C. A solution of 209 kg of 96-98% sulfuric acid in 201 kg of water is added while maintaining the temperature below 15° C. The mixture is stirred for 1 hour at this temperature and the aqueous phase is then removed (1254 kg). The organic phase is heated to 70-75° C. and 33% hydrochloric acid solution (1712 kg) is then added and the reaction mixture is refluxed for 3 hours. The medium is concentrated (250 L) and the mixture is then cooled to 50° C. and water (248 kg) is added. The aqueous phase is treated with MTBE (3×579 kg). The organic phases are combined and washed with water (257 kg). The organic phase is concentrated (821 kg distillates) and then cooled to 25° C. (S)-1-Phenylethylamine (283 kg) is added while maintaining the temperature below 25° C. The reaction mixture is cooled to 10° C. and crystallization is then initiated by adding (S)-1-phenylethylammonium (S)-2-hydroxy-2,4-dimethylpentanoate (1.3 kg). The reaction mixture is stirred overnight and then filtered. The solid is washed with MTBE (55 kg) and then dried. 108 kg of (S)-1-phenylethylammonium (S)-2-hydroxy-2,4-dimethylpentanoate are obtained.

The (S)-1-phenylethylammonium (S)-2-hydroxy-2,4-dimethylpentanoate (108 kg) and ethyl acetate (777 kg) are placed in a 1600 L reactor and the reaction mixture is then heated at 40° C. until dissolution is complete. The mixture is then cooled to 20° C. and an (S)-1-phenylethylammonium (S)-2-hydroxy-2,4-dimethylpentanoate (99% e.e.) initiator (5 g) is then introduced. The mixture is stirred for 2 hours at 20° C. and then filtered, and the cake is washed with ethyl acetate (479 kg) to give 131 kg of wet (S)-1-phenylethylammonium (S)-2-hydroxy-2,4-dimethylpentanoate (corresponding to 70.5 kg of dry (S)-1-phenylethylammonium (S)-2-hydroxy-2,4-dimethylpentanoate), which is employed in two 65.5 kg portions in the following step.

Step 2: Synthesis of
(S)-2-hydroxy-2,4-dimethylpentanoic Acid (2.2)

Wet (S)-1-phenylethylammonium (S)-2-hydroxy-2,4-dimethylpentanoate (65.5 kg) and water (100 kg) are placed in a 160 L reactor, the medium is concentrated under vacuum (50 L distillate) and is then cooled to 23° C. 34% hydrochloric acid solution (89.5 kg) is added while maintaining the temperature below 23° C. The mixture is cooled to 4° C. and then stirred for 2 hours at this temperature. The solid is filtered off and then washed with cold water (32 kg). The solid is dried under vacuum at 40° C. until the water content is less than 0.5%. This operation is repeated a second time. The two operations are combined to give (S)-2-hydroxy-2,4-dimethylpentanoic acid (18.4 kg, e.e. >99%).

1H NMR (400 MHz, DMSO-d$_6$): 12.4 (bs, 1H); 4.8 (bs, 1H); 1.74 (sept, J=6.1 Hz, 1H); 1.74 (dd, J=13.7 & 6.7 Hz, 1H); 1.46 (dd, J=13.6 & 5.6 Hz, 1H); 1.25 (s, 3H); 0.88 (d, J=6.6 Hz, 3H); 0.83 (d, J=6.6 Hz, 3H).

Example 3

Preparation of (S)-2-hydroxy-2,4-dimethylpentanoic acid (Enantioselective Method)

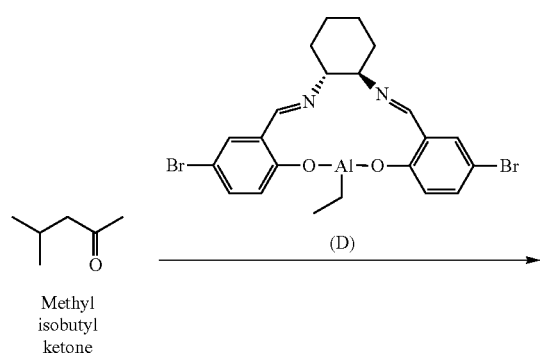

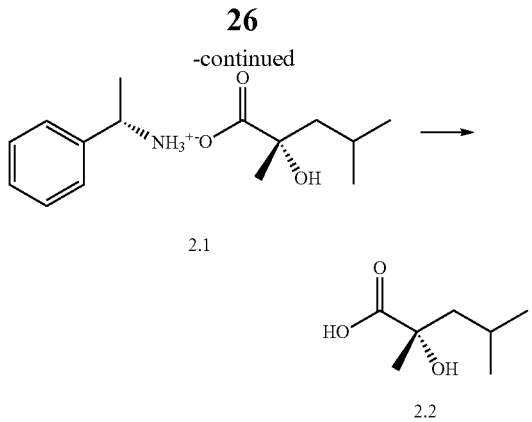

Step 1: Synthesis of (S)-1-phenylethylammonium (S)-2-hydroxy-2,4-dimethylpentanoate (2.1)

Trimethylsilyl cyanide (3161.90 ml; 24.86 mol; 0.95 eq.) and N,N-dimethylaniline oxide (8.97 g; 65.42 mmol; 0.0025 eq.) are placed in a 15 liters jacketed reactor. This solution is stirred for about 1 hour at 20-23° C.

A solution of ethylaluminum 2,2'-((1E,1'E)-(((1R,2R)-cyclohexane-1,2-diyl)bis(azanylylidene))bis(methanylylidene))bis-4-bromophenoxide (catalyst (D)) (55.92 g; 104.67 mmol; 0.004 eq.) in methyl isobutyl ketone (3276.25 ml; 26.17 mol; 1.00 eq.) and dichloromethane (7.86 L) in a 10 liter reactor is stirred for 1 hour. This solution is added to the trimethylsilyl cyanide solution at 20-23° C. and then stirred for 1 hour at this temperature. The reaction medium is concentrated to a stirrable minimum amount, and a mixture of heptane/ethyl acetate (80/20) and 1% of diisopropylethylamine (3 L) is then added. This solution is filtered through a filter packed with a thin layer of silica and then rinsed with a heptane/ethyl acetate mixture (80/20) and 1% of diisopropylethylamine (1 L). The filtrate is placed in the reactor and then concentrated under reduced pressure, to form 2,4-dimethyl-2-((trimethylsilyl)oxy)pentanenitrile in the form of a pale yellow liquid (4772 g; 91.5%).

The 2,4-dimethyl-2-((trimethylsilyl)oxy)pentanenitrile (2406 g; 12.07 mol; 1.00 eq.) and 37% hydrochloric acid solution (6 L; 72 mol; 2.50 V) are placed in a 15 liter jacketed reactor. The reaction mixture is refluxed for 5 hours. Water (6 L) is added to the reaction medium so that the internal temperature reaches about 50° C. Crystallization takes place shortly after, and the reaction mixture is then left to cool to 20-23° C. The solid is filtered off and then rinsed with water. The solid is dried in an oven at 43° C. under vacuum. (S)-2-Hydroxy-2,4-dimethylpentanoic acid (1368 g; 77%) is obtained in the form of a white crystalline powder.

(S)-2-Hydroxy-2,4-dimethylpentanoic acid (1150 g; 7.87 mol; 1.00 eq.) and ethyl acetate (11.5 L) are placed in a 15 liter jacketed reactor under nitrogen and (S)-1-phenylethylamine (912 ml; 7.08 mol; 0.90 eq.) is then added while maintaining the temperature below 30° C. Crystallization is initiated by adding 10 g of (S)-1-phenylethylammonium (S)-2-hydroxy-2,4-dimethylpentanoate. The reaction mixture is stirred for 3 hours at 20° C. and the medium is then filtered.

The solid is rinsed with ethyl acetate (1-L) and then dried in an oven at 50° C. under vacuum overnight. (S)-1-Phenylethylammonium (S)-2-hydroxy-2,4-dimethylpentanoate (1122 g; 53%) is obtained in the form of a white crystalline powder.

Step 2: Synthesis of
(S)-2-hydroxy-2,4-dimethylpentanoic acid (2.2)

(S)-1-Phenylethylammonium (S)-2-hydroxy-2,4-dimethylpentanoate (3081 g; 11.52 mol; 1.00 eq.) and water (3 L) are placed in a 15 liter jacketed reactor. 37% hydrochloric acid solution (7.7 L) is added while maintaining the temperature below 40° C. The reaction medium is cooled to 10° C. and the solid is then filtered off, washed with cold water and dried in an oven at 45° C. under vacuum. (S)-2-Hydroxy-2,4-dimethylpentanoic acid (1078 g; 64%, e.e. >99%) is obtained in the form of a white crystalline powder.
1H NMR (400 MHz, DMSO-$d_6$): 12.4 (bs, 1H); 4.8 (bs, 1H); 1.74 (sept, J=6.1 Hz, 1H); 1.74 (dd, J=13.7 & 6.7 Hz, 1H); 1.46 (dd, J=13.6 & 5.6 Hz, 1H); 1.25 (s, 3H); 0.88 (d, J=6.6 Hz, 3H); 0.83 (d, J=6.6 Hz, 3H).

Example 4

Preparation of (S)—N-(2-bromo-6-methoxypyrid-4-yl)-2-hydroxy-2,4-dimethylpentanamide

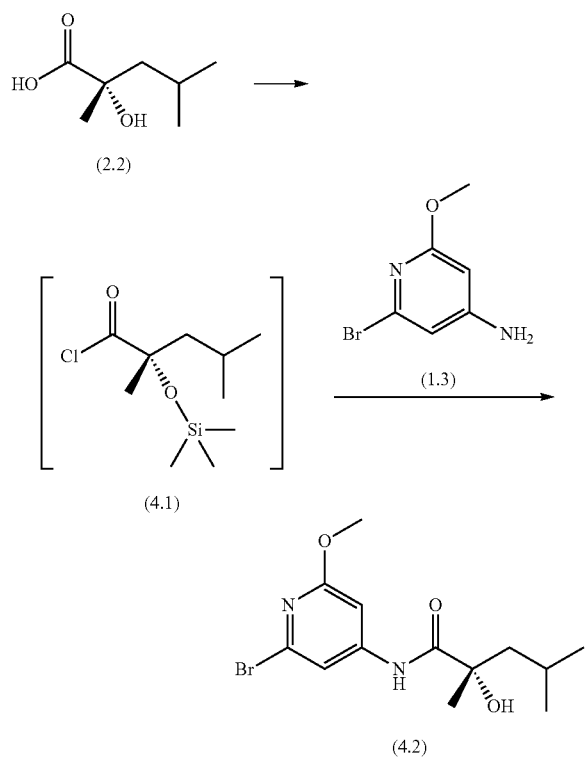

(S)-2-Hydroxy-2,4-dimethylpentanoic acid (3073 g; 21 mol; 1.00 eq.), 4-dimethylaminopyridine (128 g; 1 mol; 0.05 eq.) and dichloromethane (24.5 L) are placed in a 100 L reactor. The reaction mixture is cooled to about 0° C. Pyridine (3.75 L) and dichloromethane (6 L) are added while maintaining the temperature at 0-5° C.
Trimethylchlorosilane (5.8 L; 46 mol; 2.20 eq.) is added while maintaining the temperature below 5° C. The reaction mixture is warmed to 20° C. and stirred for 4 hours 30 minutes at this temperature, and then cooled to 0° C. N,N-Dimethylformamide (55 ml; 0.71 mol; 0.03 eq.) is added while maintaining the temperature below 5° C., and oxalyl chloride (1622 ml; 18.9 mol; 0.90 eq.) is then added while maintaining the temperature below 5° C. The reaction mixture is stirred for 1 hour at this temperature and N,N-dimethylformamide (27.50 ml; 0.36 mol; 0.02 eq.) is then added. The reaction mixture is warmed to about 20° C. and stirred for 1 hour at this temperature.
A solution of 2-bromo-4-amino-6-methoxypyridine (3543 g; 17.4 mol; 0.83 eq.) in a dichloromethane (27.3 L)/pyridine (1.9 L) mixture is added to the preceding solution while maintaining the temperature below 25° C. The reaction mixture is stirred for 30 minutes at this temperature. The reaction progress is monitored by TLC with 5% control.
A solution of acetic acid (23 L; 41 mol; 1.95 eq.) in ethanol (19 L) is prepared in a new disposable container of suitable volume and then poured into the reaction mixture while maintaining the temperature below 25° C. The reaction medium is stirred overnight at about 20° C. The reaction progress is monitored by TLC.
An aqueous solution of hydrochloric acid (2.4 L; 12.00 M; 28.77 mol; 0.78 V) in water (27 L) is prepared in a new disposable container of suitable volume and then poured into the reaction medium and stirred for 10 minutes. The aqueous phase is discarded and the organic phase is then washed with water (30 L). The aqueous phase is discarded and the organic phase is then washed again with a solution prepared from NaOH (1 177.29 g; 29.43 mol; 1.40 eq.) in water (30 L). The aqueous phase is discarded and the organic phase is then washed again with water (30 L).
The aqueous phase is discarded. The organic phase is clarified on a filter packed with active charcoal (921 g) and the cake is then washed with dichloromethane (10 L). The filtrate is then placed in the reactor and concentrated at reflux, distillate (37 L). Cyclohexane (43 L) is added to the reactor, which is then refluxed until the head temperature reaches 75° C. (distilled volume 22.5 L). Cyclohexane (10 L) is added and the reactor is allowed to cool to 27° C. An (S)—N-(2-bromo-6-methoxypyrid-4-yl)-2-hydroxy-2,4-dimethylpentanamide initiator (138 g; 0.42 mol; 0.02 eq.) is added to promote the crystallization. The reaction mixture is cooled to 20° C. and then filtered through a 25 μm filter gauze.
The reactor and the filter are rinsed with cyclohexane (10 L). The solid is dried in an oven at 45° C. under vacuum to give (S)—N-(2-bromo-6-methoxypyrid-4-yl)-2-hydroxy-2,4-dimethylpentanamide (3.7 kg; 65%).
1H NMR (400 MHz, DMSO-$d_6$): 10.0 (bs, 1H); 7.73 (s, 1H); 7.33 (s, 1H); 5.70 (bs, 1H); 3.80 (s, 3H); 1.79-1.67 (m, 2H); 1.49 (dd, J=13.6 & 5.2 Hz, 1H); 1.32 (s, 3H); 0.89 (d, J=6.4 Hz, 3H); 0.78 (d, J=6.4 Hz, 3H)

Comparative Example 1

Attempted Preparation of N-(2-bromo-6-methoxypyrid-4-yl)-2-hydroxy-2-ethylhexanamide

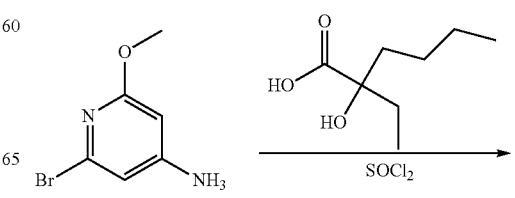

-continued

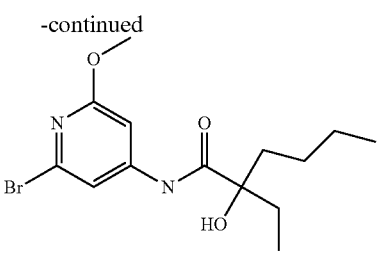

500 mg (2.46 mmol, 1 equiv.) of 2-bromo-4-amino-6-methoxypyridine are placed in a one-necked 50 mL round-bottomed flask and 20 mL of toluene and 586 mg (4.92 mmol, 2 equiv.) of thionyl chloride are added. The mixture is then refluxed for 3 hours. The product is then concentrated to dryness and is redissolved in 20 mL of acetonitrile. 1.6 mg (9.79 mmol, 4 equiv.) of 2-ethyl-2-hydroxyhexanoic acid are added and the mixture is heated at 70° C. for 16 hours.

Liquid-phase chromatography combined with mass analysis shows that the reaction has not taken place. The test is thus stopped.

Comparative Example 2

Attempted Preparation of (S)—N-(2-bromo-6-methoxypyrid-4-yl)-2-hydroxy-2,4-dimethylpentanamide

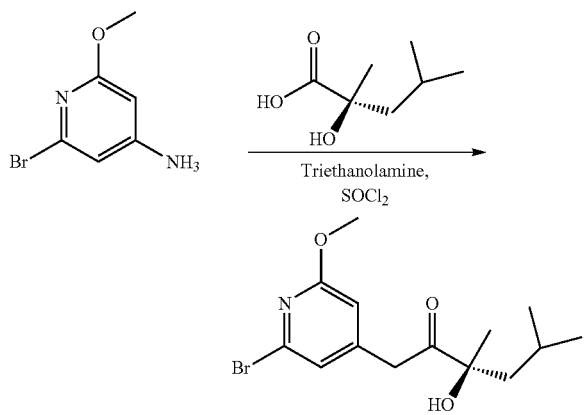

1.00 g (4.93 mmol, 1 equiv.) of 2-bromo-4-amino-6-methoxypyridine is placed in a 100 ml three-necked round-bottomed flask and 5 mL of acetonitrile, 716.85 µL (5.17 mmol, 1.05 equiv.) of triethanolamine and 413.3 µl (5.66 mmol, 1.15 equiv.) of thionyl chloride are added, while taking care not to exceed an internal temperature of 20° C. (the addition of thionyl chloride is exothermic). The reaction medium turns a bright yellow color.

The medium is then stirred at room temperature for 2 hours.

A solution of (S)—N-(2-bromo-6-methoxypyrid-4-yl)-2-hydroxy-2,4-dimethylpentanamide (0.83 g, 5.66 mmol, 1.15 equiv.) in acetonitrile (10.0 mL) is prepared.

The solution is then added to the reaction medium. The addition funnel is rinsed with acetonitrile. The reaction medium is stirred at room temperature.

A first control is performed by liquid-phase chromatography (HPLC) combined with mass analysis after 1 hour. The desired final product is not detected. Only the starting materials are detected.

The reaction medium is stirred overnight at room temperature, after which a second control is performed.

The desired final product is not detected. Only the starting materials are detected. The test is thus stopped.

These comparative examples show that by using standard conditions (trialkylamine and thionyl chloride), commonly used in the prior art, there is no formation of the amide.

In order for the amide to form, it is necessary to use a halotrialkylsilane as described in example 4 of the patent application.

The invention claimed is:
1. A process for preparing an enantiomerically pure compound corresponding to the general formula (C):

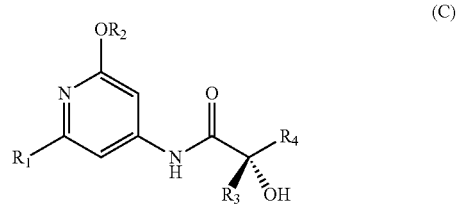

in which:
R$_1$ represents a halogen atom;
R$_2$ represents a C$_1$-C$_4$ alkyl;
R$_3$ represents a C$_1$-C$_2$ alkyl;
R$_4$ represents a C$_3$-C$_6$ alkyl;
according to a process comprising the following successive steps:
a) reacting in a halogenated solvent a chiral α-hydroxy acid intermediate of formula (A):

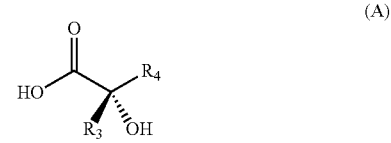

in the presence of a halotrialkylsilane and an organic amine base;
b) adding N,N-dimethylformamide and a carboxylic acid chlorinating agent at a temperature of from 0° C. to 5° C.;
c) adding an aromatic intermediate of formula (B):

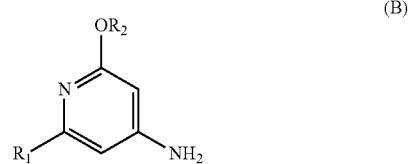

as a solution in a halogenated solvent in the presence of an organic amine base;
d) adding an organic or mineral acid dissolved in an alcohol;
e) treating the reaction medium obtained in step d), comprising:
  i. performing decantation followed by filtration of the organic phase over active charcoal; and ii. performing crystallization, following the addition of a saturated hydrocarbon, of the enantiomerically pure compound corresponding to the general formula (C).

2. The process according to claim 1, wherein $R_1$ is a bromine atom, $R_2$ is a methyl, $R_3$ is a methyl and $R_4$ is an isobutyl.

3. The process according to claim 1, wherein the halotrialkylsilane and the organic amine base used in step a) are, respectively, trimethylsilyl chloride and 4-dimethylaminopyridine.

4. The process according to claim 1, wherein the carboxylic acid chlorinating agent used in step b) is oxalyl chloride.

5. The process according to claim 1, wherein the saturated hydrocarbon used in step e) ii is cyclohexane.

6. The process according to claim 1, wherein $R_1$ is bromine.

7. The process according to claim 1, wherein $R_2$ is a methyl.

8. The process according to claim 1, wherein $R_3$ is a methyl.

9. The process according to claim 1, wherein $R_4$ is an isobutyl.

* * * * *